United States Patent
Dukhande et al.

(10) Patent No.: US 11,602,737 B2
(45) Date of Patent: Mar. 14, 2023

(54) METAL HYDROXIDE BASED IONIC LIQUID COMPOSITION

(71) Applicant: RELIANCE INDUSTRIES LIMITED, Maharashtra (IN)

(72) Inventors: Vibhuti Dukhande, Maharashtra (IN); Parasu Veera Uppara, Maharashtra (IN); Pavankumar Aduri, Maharashtra (IN); Vivek Prabhakar Raje, Maharashtra (IN); Prathmesh Pradeep Salvi, Maharashtra (IN); Viswanath Kotra, Andhra Pradesh (IN); Mangesh Sakhalkar, Maharashtra (IN); Uday Meghashyam Ratnaparkhi, Maharashtra (IN)

(73) Assignee: RELIANCE INDUSTRIES LIMITED, Maharashtra (IN)

( * ) Notice: Subject to any disclaimer, the term of this patent is extended or adjusted under 35 U.S.C. 154(b) by 311 days.

(21) Appl. No.: 16/840,375

(22) Filed: Apr. 4, 2020

(65) Prior Publication Data
US 2020/0238261 A1    Jul. 30, 2020

Related U.S. Application Data

(63) Continuation-in-part of application No. 15/772,206, filed as application No. PCT/IB2016/056645 on Nov. 4, 2016, now abandoned.

(30) Foreign Application Priority Data

Nov. 5, 2015  (IN) .......................... 4217/MUM/2015

(51) Int. Cl.
| | | |
|---|---|---|
| *B01J 27/10* | (2006.01) | |
| *B01J 27/128* | (2006.01) | |
| *B01J 23/72* | (2006.01) | |
| *B01J 23/745* | (2006.01) | |
| *B01J 21/04* | (2006.01) | |
| *B01J 31/26* | (2006.01) | |
| *B01J 31/30* | (2006.01) | |

(52) U.S. Cl.
CPC ............... *B01J 27/10* (2013.01); *B01J 21/04* (2013.01); *B01J 23/72* (2013.01); *B01J 23/745* (2013.01); *B01J 27/128* (2013.01); *B01J 31/26* (2013.01); *B01J 31/30* (2013.01)

(58) Field of Classification Search
CPC ............. B01J 27/10; B01J 31/26; B01J 31/30
See application file for complete search history.

(56) References Cited

U.S. PATENT DOCUMENTS

| | | | |
|---|---|---|---|
| 4,624,755 A | | 11/1986 | McManis, III et al. |
| 6,096,680 A | * | 8/2000 | Park ...................... C07C 7/152 |
| | | | 502/169 |
| 2004/0054231 A1 | | 3/2004 | Abbott et al. |
| 2010/0204529 A1 | | 8/2010 | Terada et al. |
| 2011/0124930 A1 | | 5/2011 | Smith et al. |
| 2013/0211175 A1 | * | 8/2013 | Timken ................... A62D 3/35 |
| | | | 588/318 |
| 2016/0346816 A1 | * | 12/2016 | Timken ................... C22B 7/009 |
| 2017/0137380 A1 | * | 5/2017 | Rodrigues ............. A61L 27/227 |

FOREIGN PATENT DOCUMENTS

| | | | |
|---|---|---|---|
| CN | 102099319 A | | 6/2011 |
| CN | 102441433 A | * | 5/2012 |
| CN | 104815683 A | | 8/2015 |
| WO | 2007/003956 A2 | | 1/2007 |

OTHER PUBLICATIONS

Machine translation of CN102441433A, publication date May 2012.*
International Search Report of PCT/IB2016/056645, dated Jan. 19, 2017.
Bermúdez, "Introduction to the Ionic Liquids Special Issue", Tribol Lett, Springer Science+Business Media, LLC 2010, published Oct. 12, 2010, p. 213 (1 page).
Jacquemin et al., "Introduction on Special Issue: Ionic Liquids", J Solution Chem, Springer Science+Business Media New York 2015, published Mar. 28, 2015, pp. 379-381 (3 pages).

* cited by examiner

*Primary Examiner* — Jun Li
(74) *Attorney, Agent, or Firm* — Collard & Roe, P.C.

(57) ABSTRACT

The present disclosure relates to an ionic liquid composition and a process for its preparation. The process of the present disclosure is simple, single pot and efficient process for preparing the ionic liquid composition which is effective in a Friedel Craft reaction like, alkylation reaction, trans-alkylation, and acylation.

The present disclosure envisages an ionic liquid composition comprising at least one metal hydroxide; at least one metal halide; and at least one solvent. Also envisaged is a process for preparing an ionic liquid composition. The process comprises mixing in a reaction vessel, at least one metal hydroxide and at least one metal halide in the presence of at least one solvent under a nitrogen atmosphere and continuous stirring followed by cooling under continuous stirring to obtain the ionic liquid composition.

7 Claims, No Drawings

METAL HYDROXIDE BASED IONIC LIQUID COMPOSITION

CROSS REFERENCE TO RELATED APPLICATIONS

This application is a continuation in part application of U.S. patent application Ser. No. 15/772,206 filed on Apr. 30, 2018 wherein that application is a National stage application of PCT/162016/056645 filed on Nov. 4, 2016 wherein that application claims priority to IN4217/MUM/2015 filed on Nov. 5, 2015 the disclosures of all of these applications are hereby incorporated herein by reference in their entirety.

FIELD

The present disclosure relates to an ionic liquid composition and a process for its preparation.

Definitions

As used in the present disclosure, the following terms are generally intended to have the meaning as set forth below, except to the extent that the context in which they are used indicate otherwise.

The expression 'Clathrate' for the purpose of the present disclosure refers to a chemical substance consisting of a lattice that traps or contains molecules.

The expression 'Eutectic' for the purpose of the present disclosure refers to a system that describes a homogeneous solid mix of atomic and/or chemical species, to form a joint super-lattice, by striking a unique atomic percentage ratio between the components; as each pure component has its own distinct bulk lattice arrangement.

BACKGROUND

Ionic liquids are composed entirely of ions or a combination of cations and anions. The most common ionic liquids are those prepared from organic-based cations and inorganic or organic anions. The most common organic cations are ammonium cations, phosphonium and sulphonium cations. Ionic liquids of pyridinium and imidazolium are perhaps the most commonly used cations. Anions include, but are not limited to $BF_4^-$, $PF_6^-$, haloaluminates such as $Al_2Cl_7^-$ and $Al_2Br_7^-$, $[(CF_3SO_2)_2N]^-$, alkyl sulphates ($RSO^{3-}$), carboxylates ($RCO_2^-$) and many others. The most catalytically interesting ionic liquids are those derived from ammonium halides and Lewis acids (such as $AlCl_3$, $TiCl_4$, $SnCl_4$, $FeCl_3$ and the like). Chloroaluminate ionic liquids are perhaps the most commonly used ionic liquid catalyst systems. Ionic liquids may be suitable, for example, for use as catalysts and as solvents in alkylation and polymerization reactions as well as in dimerization, oligomerization acetylation, metatheses, and copolymerization reactions. Various methods have been mentioned for the preparation of ionic liquids. For example, ionic liquids can be prepared from organic cations and anions that can coordinate to the metal ions and by the addition of Lewis acid to Lewis base.

Further, "low temperature" ionic liquids are generally salts having melting point lower than 100° C., often even lower than room temperature. Further, some ionic liquids are fused salt compositions, which are molten at low temperature and are useful as catalysts, solvents, and electrolytes. Such compositions are mixtures of components which are liquids at temperatures below the individual melting points of the components.

The conventionally known "low temperature" ionic liquids are less effective when used as catalysts in the alkylation reactions. Further, these known ionic liquids are expensive. Still further, the acidity of the conventionally known ionic liquids are not tunable.

There is, therefore, felt a need for a cost-effective ionic liquid composition which can be effectively used in alkylation reaction.

Objects

Some of the objects of the present disclosure, which at least one embodiment herein satisfies, are as follows:

It is an object of the present disclosure to ameliorate one or more problems of the prior art or to at least provide a useful alternative.

An object of the present disclosure is to provide an ionic liquid composition that can be effectively used in alkylation, trans-alkylation, and acylation reactions.

Another object of the present disclosure is to provide a process for preparing an ionic liquid composition having a desired viscosity and density.

Other objects and advantages of the present disclosure will be more apparent from the following description, which is not intended to limit the scope of the present disclosure.

SUMMARY

The present disclosure envisages an ionic liquid composition comprising at least one metal hydroxide; at least one metal halide; and at least one solvent. Typically, the metal hydroxide is present in an amount ranging from 3% to 40% by weight of the composition; the metal halide is present in an amount ranging from 8% to 90% by weight of the composition; and the solvent is present in an amount ranging from 10% to 70% by weight of the composition. Also envisaged is a process for preparing an ionic liquid composition. The process comprises mixing in a reaction vessel, at least one metal hydroxide and at least one metal halide in the presence of at least one solvent a under nitrogen atmosphere and continuous stirring to obtain a mixture. This mixture is then kept in a water bath at a temperature in the range of 80 to 120° C. under continuous stirring at 800 rpm for 4 hours to obtain a reaction mixture, followed by cooling the reaction mixture under continuous stirring at 800 rpm to obtain the ionic liquid composition in the form of an ionic liquid clathrate.

Typically, the solvent is selected from the group consisting of benzene, toluene, xylene, chlorobenzene, bromobenzene, substituted benzenes and ethylene dichloride. Typically, the metal of the metal hydroxide and the metal of at least one metal halide are same or are different. Typically, the metal of the metal hydroxide is selected from the group consisting of S-block metals, P-block metals and transition metals; wherein the metal of the metal hydroxide is selected from the group consisting of Al, Cr, Mn, Fe, Co, Ni, Cu, Zn, Ga, Ge, In, Sn, Ti, Pb, Cd, and Hg.

Typically, the metal of the metal halide is selected from the group consisting of transition metals and P-block metals; wherein the metal of the at least one metal halide is selected from the group consisting of Al, Cr, Mn, Fe, Co, Ni, Cu, Zn, Ga, Ge, In, Sn, Ti, Pb, Cd, and Hg. Typically, the halide is selected from the group consisting of chloride, bromide, fluoride and iodide.

In an embodiment of the present disclosure, the ionic liquid composition has a viscosity ranging from 3 cP to 500 cP and density ranging from 1.00 to 2.50.

DETAILED DESCRIPTION

Ionic liquids are entirely composed of ions. The so-called "low temperature" Ionic liquids are generally salts with melting point under 100° C., or even lower than room temperature. Such "low temperature ionic liquids" may be suitable as catalysts and as solvents in alkylation and polymerization reactions. The "low temperature ionic liquids" are also suitable in dimerization, oligomerization acetylation, metatheses, and copolymerization reactions. The conventionally known "low temperature" ionic liquid composition are less effective when used as catalysts in the alkylation reactions. Further, these known ionic liquid catalysts are expensive. Still further, the acidity of the conventionally known "low temperature" ionic liquids is not steady.

Therefore, the inventors of the present disclosure envisage an ionic liquid composition, and a process for preparing the ionic liquid composition that can be used in all Friedel Crafts reactions like, alkylation, reaction and that has a desired acidity.

In one aspect, the present disclosure envisages an ionic liquid composition.

The composition of the present disclosure, comprises at least one metal hydroxide, at least one metal halide, and at least one solvent.

In an embodiment of the present disclosure, the metal of the halides and the metal of the hydroxides are the same or different.

In yet another embodiment of the present disclosure, the solvent is at least one selected from the group consisting of benzene, toluene, xylene, chlorobenzene, substituted benzenes, and ethylene dichloride. Typically, the amount of solvent used in the ionic liquid composition is in the range of 10% to 70% by weight.

In an embodiment of the present disclosure, the metal of the metal halides is selected from the group consisting of transition metals and P-block metals. Typically, the metal of the metal halides, is at least one selected from the group consisting of Al, Cr, Mn, Fe, Co, Ni, Cu, Zn, Ga, Ge, In, Sn, Ti, Pb, Cd, and Hg. Typically the halide is at least one selected from the group consisting of chloride, bromide, fluoride and iodide.

In one embodiment of the present disclosure, the metal halide is at least one selected from the group consisting of $AlCl_3$, $FeCl_3$, $GaCl_3$, $InCl_3$, $TiCl_4$, $SnCl_4$, $BiCl_3$, and $ZrCl_4$.

In an embodiment of the present disclosure, the metal of the hydroxides is selected from the group consisting of S-block metals, P-block metals and transition metals. Typically, the metal of the metal hydroxides, is at least one selected from the group consisting of Al, Cr, Mn, Fe, Co, Ni, Cu, Zn, Ga, Ge, In, Sn, Ti, Pb, Cd, and Hg.

Typically, the amount of metal hydroxide used may be varied in order to obtain an ionic liquid of the desired acidity.

In one embodiment of the present disclosure, the metal hydroxide is at least one selected from the group consisting of $Al(OH)_3$, $Fe(OH)_3$, and $Zn(OH)_2$.

In an embodiment of the present disclosure, the ionic liquid composition comprises at least one metal hydroxide in an amount ranging from 3% to 40% by weight of the composition; at least one metal halide in an amount ranging from 8% to 90% by weight of the composition; and at least one solvent in an amount ranging from 10% to 70% by weight of the composition. Typically, the solvent is selected from the group consisting of benzene, toluene, xylene, chlorobenzene, bromobenzene, substituted benzenes and ethylene dichloride.

In another embodiment of the present disclosure, the viscosity of the ionic liquid composition ranges from 3 cP to 500 cP and density of the ionic liquid composition ranges from 1.00 to 2.50.

In yet another embodiment of the present disclosure, 1 mole of metal hydroxide reacts with 1 or more moles of metal halide in the presence of at least one aromatic solvent, under heating to form the ionic liquid composition.

Typically, the ionic liquid composition is formed by the same or different metals and the process may be applied to any metal hydroxide and to any metal halide.

In another aspect, the present disclosure envisages a process for the preparation of the ionic liquid composition. The process of the present disclosure is a single pot synthesis process; using at least one metal hydroxide, at least one metal halide, and at least one solvent.

The process of preparation of the ionic liquid composition comprises the step of mixing at least one metal hydroxide and at least one metal halide in at least one solvent under continuous stirring at a temperature in the range of 5° C. to 200° C. to obtain the ionic liquid composition. The ionic liquid composition of the present disclosure is in the form of ionic liquid clathrate.

The ionic liquid clathrate obtained from the process of the present disclosure is a metal hydroxide based clathrate. The clathrate is a chemical substance consisting of a lattice that traps or contains molecules of solvent in the metal hydroxide and metal halide ionic liquid.

In an exemplary embodiment 1 mole of aluminium hydroxide is heated with 1.5 moles $AlCl_3$ in the presence of benzene at 80° C. to obtain a eutectic mixture containing the ionic liquid composition.

The process of preparing a metal hydroxide based ionic liquid composition (ionic liquid clathrate) can be represented by the following general formulae—

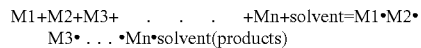

Wherein, M1 is metal hydroxide, M2, M3, . . . , Mn are metal halides. M1, M2, M3, . . . , Mn contain metals which may be the same or different and n may range from 2 to 20. The dot (•) between M1, M2, M3, Mn and solvent represents at least one of coordinate covalent bonds and weak van der waal forces, and therefore the product forms an ionic liquid/eutectic mixture wherein the components are not ordinarily separable and take part in a reaction as a catalyst as a whole.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTS

Experiment-1: Preparation of the Ionic Liquid Composition 100 ml of clean and dry three necked round bottom flask (RBF) was taken for the experiment. The center neck of the round bottom flask was used for overhead stirring using a glass stirrer, the other neck was mounted with a reflux condenser with nitrogen atmosphere, and the remaining neck was used for dispensing raw materials. The RBF was placed in a water bath at room temperature (25-30° C.) and the coolant flow was kept at 5° C. in the reflux condenser. 20 ml dry benzene was transferred into RBF by using a funnel and was stirred at 200 rpm. 2 g anhydrous Al(OH)$_3$ powder was added into the round bottom flask using an additional funnel. The addition was carried out under continuous stirring and maintained for 10 min at 300 rpm. 10.2 g AlCl$_3$ was added continuously into the round bottom flask by using an additional funnel in a batch of 2.50 g each. Stirring was continued for 5 min. After stirring the reaction mixture for 5 min, the temperature of the water bath was increased to 80° C. The reaction mixture was stirred vigorously at 800 rpm for 4 hrs at 80° C., until no solids appeared in the RBF. Once the reaction mixture was dark brown in color, with no solid deposition in it, heating was stopped and stirring was continued at 800 rpm. The reaction mixture was cooled to 30° C. and the so obtained product was stored in air tight container, under N$_2$ atmosphere.

Similar experiments can be carried out and product can be obtained using metal hydroxides of Al, Cr, Mn, Fe, Co, Ni, Cu, Zn, Ga, Ge, In, Sn, Ti, Pb, Cd, and Hg, and metal halides of Al, Cr, Mn, Fe, Co, Ni, Cu, Zn, Ga, Ge, In, Sn, Ti, Pb, Cd, and Hg. Particularly, metal hydroxides are Al(OH)$_3$, Fe(OH)$_3$, and Zn(OH)$_2$. Further the solvents may be selected from the group consisting of benzene, toluene, xylene, chlorobenzene, bromobenzene, substituted benzenes and ethylene dichloride.

Experiments 2-32 were performed similar to the experiment 1, except the variation in the reactants (metal hydroxide, metal halide and solvent) and their qunatities:

Experiment 2

3.12 g Aluminum Hydroxide was taken in three neck round bottom flask, 18.32 g Benzene was added in the flask to obtain a mixture. The mixture of hydroxide and benzene was stirred at room temperature (25-30° C.) for 10 min. 1.9 g anhydrous Magnesium chloride was slowly added to the RBF. The reactor assembly was kept in water bath and heated to 80° C. and further stirred for 3 hrs to obtain a dark brown coloured liquid product.

Experiment 3

3.12 g Aluminium Hydroxide was taken in three neck round bottom flask, 19.5 g Benzene was added in the flask to obtain a mixture. The mixture of hydroxide and benzene was stirred at room temperature (25-30° C.) for 10 min. 13.3 g anhydrous copper chloride and 13.3 g anhydrous Aluminium Chloride were slowly added to the RBF, The reactor assembly was kept in water bath and heated to 80° C. and further stirred for 3 hrs to obtain a dark brown coloured liquid product.

Experiment 4

1.56 g Aluminum Hydroxide was taken in three neck round bottom flask, 9.83 g Benzene was added in the flask to obtain a mixture. The mixture of hydroxide and benzene was stirred at room temperature (25-30° C.) for 10 min. 6.65.g anhydrous Magnesium chloride and 1.62 g Ferric chloride were slowly added to the RBF. The reactor assembly was kept in water bath and heated to 80° C. and further stirred for 3 hrs to obtain a dark brown coloured liquid product.

Experiment 5

1.56 g Aluminium Hydroxide was taken in three neck round bottom flask, 9.57 g Benzene was added in the flask to obtain a mixture. The mixture of hydroxide and benzene was stirred at room temperature (25-30° C.) for 10 min. 6.65.g anhydrous Magnesium chloride and 1.36 g Zinc chloride were added slowly to the RBF. The reactor assembly was kept in water bath and heated to 80° C. and further stirred for 3 hrs to obtain a dark brown coloured liquid product.

Experiment 6

1.56 g Ferric Hydroxide was taken in three neck round bottom flask, 9.57 g Benzene was added in the flask to obtain a mixture. The mixture of hydroxide and benzene was stirred at room temperature (25-30° C.) for 10 min. 5.83 g anhydrous Aluminium chloride was slowly added to the RBF. The reactor assembly was kept in water bath and heated to 80° C. and further stirred for 3 hrs to obtain a dark brown coloured liquid product.

Experiment 7

2 g copper Hydroxide was taken in three neck round bottom flask, 9.57 g Benzene was added in the flask to obtain a mixture. The mixture of hydroxide and benzene was stirred at room temperature (25-30° C.) for 10 min. 8.2 g anhydrous aluminum chloride was slowly added to the RBF. The reactor assembly was kept in water bath and heated to 80° C. and further stirred for 3 hrs to obtain a dark brown coloured liquid product.

Experiment 8

1 g anhydrous Aluminium hydroxide and 0.45 g of ferric hydroxide was taken in three neck round bottom flask. 20 g of Benzene added in the flask to obtain a mixture. The mixture of hydroxide and benzene was stirred at room temperature (25-30° C.) for 10 min. Dry anhydrous 7.3 g Aluminium chloride was slowly added to the reaction mixture. Temperature of reaction mixture was raised to 80° C. and benzene kept under reflux and further stirred for 3 hr to get homogeneous dark colour liquid.

Experiment 9

1 g anhydrous Ferric hydroxide was taken in three neck round bottom flask. 15 g of Benzene added in the flask to obtain a mixture. The mixture of hydroxide and benzene was stirred at room temperature (25-30° C.) for 10 min. Dry anhydrous 3.4 g Aluminium chloride and anhydrous 0.37 g ferric chloride was slowly added to the reaction mixture. Temperature of reaction mixture was raised to 80° C. and benzene kept under reflux and further stirred for 3 hr to get homogeneous dark colour liquid.

Experiment 10

1 g anhydrous Aluminium hydroxide and 0.31 g of cupric hydroxide was taken in three neck round bottom flask. 15 g of Benzene used added in the flask to obtain a mixture. Mixture of hydroxide and benzene was stirred at room temperature (25-30° C.) for 10 min. Dry anhydrous 7.26 g Aluminium chloride was slowly added to the reaction mixture. Temperature of reaction mixture was raised to 80° C. and benzene kept under reflux and further stirred for 3.5 hr to get homogeneous dark colour liquid.

Experiment 11

1 g anhydrous Aluminium hydroxide was taken in three neck round bottom flask. 15 g of Benzene added in the flask to obtain a mixture. The mixture of hydroxide and benzene was stirred at room temperature (25-30° C.) for 10 min. Dry anhydrous 4.7 g Aluminium chloride, anhydrous 0.31 g Cuprous chloride and anhydrous 0.43 g Cupric chloride was slowly added to the reaction mixture. Temperature of reaction mixture was raised to 80° C. and benzene kept under reflux and further stirred for 3 hr to get homogeneous dark colour liquid.

Experiment 12

1 g anhydrous chromium hydroxide was taken in three neck round bottom flask. 15 g of Benzene added in the flask to obtain a mixture. The mixture of hydroxide and benzene was stirred at room temperature (25-30° C.) for 10 min. Dry anhydrous 2.58 g Aluminium chloride and anhydrous 2.3 g chromium chloride was slowly added to the reaction mixture. Temperature of reaction mixture was raised to 80° C. and benzene kept under reflux and further stirred for 3 hr to get homogeneous dark purple colour liquid.

Experiment 13

1 g anhydrous nickel hydroxide was taken in three neck round bottom flask. 25 g of Benzene added in the flask to obtain a mixture. The mixture of hydroxide and benzene was stirred at room temperature (25-30° C.) for 10 min. Dry anhydrous 3.8 g Aluminium chloride and anhydrous 0.6 g titanium tetrachloride was slowly added to the reaction mixture. Temperature of reaction mixture was raised to 80° C. and benzene kept under reflux and further stirred for 3 hr to get homogeneous dark colour liquid.

Experiment 14

1 g anhydrous Aluminium hydroxide and 0.83 g of copper hydroxide was taken in three neck round bottom flask. 20 g of Benzene added in the flask to obtain a mixture. The mixture of hydroxide and benzene was stirred at room temperature (25-30° C.) for 10 min. Dry anhydrous 12.13 g ferric chloride was slowly added to the reaction mixture. Temperature of reaction mixture was raised to 80° C. and benzene kept under reflux and further stirred for 3.5 hr to get homogeneous dark colour liquid.

Experiment 15

1 g anhydrous Ferric hydroxide was taken in three neck round bottom flask. 15 g of Benzene added in the flask to obtain a mixture. The mixture of hydroxide and benzene was stirred at room temperature (25-30° C.) for 10 min. Dry anhydrous 3.03 g ferric chloride and anhydrous 1.48 g chromium chloride was slowly added to the reaction mixture. Temperature of reaction mixture was raised to 80° C. and benzene kept under reflux and further stirred for 3 hr to get homogeneous dark colour liquid.

Experiment 16

1 g anhydrous Aluminium hydroxide and 0.29 g of nickel hydroxide was taken in three neck round bottom flask. 20 g of Benzene added in the flask to obtain a mixture. The mixture of hydroxide and benzene was stirred at room temperature (25-30° C.) for 10 min. Dry anhydrous 6.4 g Aluminium chloride was slowly added to the reaction mixture. Temperature of reaction mixture was raised to 80° C. and benzene kept under reflux and further stirred for 3.5 hr to get homogeneous dark colour liquid.

Experiment 17

1 g anhydrous Aluminium hydroxide and 0.13 g of cupric hydroxide was taken in three neck round bottom flask. 20 g of Benzene added in the flask to obtain a mixture. The mixture of hydroxide and benzene was stirred at room temperature (25-30° C.) for 10 min. Dry anhydrous 5.8 g Aluminium chloride was slowly added to the reaction mixture. Temperature of reaction mixture was raised to 80° C. and benzene kept under reflux and further stirred for 3.5 hr to get homogeneous dark colour liquid.

Experiment 18

1 g anhydrous Aluminium hydroxide and 0.16 g of lead hydroxide was taken in three neck round bottom flask. 20 g of Benzene added in the flask to obtain a mixture. The mixture of hydroxide and benzene was stirred at room temperature (25-30° C.) for 10 min. Dry anhydrous 5.3 g Aluminium chloride was slowly added to the reaction mixture. Temperature of reaction mixture was raised to 80° C. and benzene kept under reflux and further stirred for 3.5 hr to get homogeneous dark colour liquid.

Experiment 19

1 g anhydrous Aluminium hydroxide was taken in three neck round bottom flask. 15 g of Benzene added in the flask to obtain a mixture. The mixture of hydroxide and benzene was stirred at room temperature (25-30° C.) for 10 min. Dry anhydrous 1.7 g Aluminium chloride and anhydrous 6.8 g Aluminium Bromide was slowly added to the reaction mixture. Temperature of reaction mixture was raised to 80° C. and benzene kept under reflux and further stirred for 3.5 hr to get homogeneous dark colour liquid.

Experiment 20

1 g anhydrous g anhydrous ferric hydroxide was taken in three neck round bottom flask. 15 g of Benzene added in the flask to obtain a mixture. The mixture of hydroxide and benzene was stirred at room temperature (25-30° C.) for 10 min. Dry anhydrous 4.15 g ferric chloride and anhydrous 3.41 g Aluminium Bromide was slowly added to the reaction mixture. Temperature of reaction mixture was raised to 80° C. and benzene kept under reflux and further stirred for 3.5 hr to get homogeneous dark colour liquid.

Experiments 21-32

Experiments 21-32 were carried out in a similar procedure as in experiments 8-18 respectively, except benzene was replaced by toluene and the reaction temperature was raised to 110° C. after complete addition of raw material.

Experiment: Alkylation Reaction 0.52 litre of hydrocarbon stream containing 10-13% C10-C14 olefins & 87-90% paraffins and 0.202 litre of benzene were charged into a 2.50 L glass reactor. The glass reactor was kept under an overhead stirrer in a heating mantle. $N_2$ flow was ensured inside the reactor. The reactor was then heated to 38-39° C. Once this temperature was achieved, 7 g of the ionic liquid composition prepared as per experiment-1 was added (as a catalyst) to the reactor and stirred for 5 minutes. After 5 minutes the reaction mass was allowed to settle for 10 minutes. The upper hydrocarbon layer was then analyzed. The conversion of benzene into linear alkyl benzene was found to be 98%.

Technical Advancements

The present disclosure described herein above has several technical advantages including, but not limited to, the realization of:

simple, single pot and efficient process for preparing an ionic liquid composition;

an ionic liquid composition which is effective in a Friedel Craft reaction like, alkylation reaction, trans-alkylation, and acylation;

an ionic liquid composition that has tunable acidity; and an ionic liquid composition that has a desired viscosity and density.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions, and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

What is claimed is:

1. A process for preparing an ionic liquid composition, said process comprising the following steps:
    using a single reaction vessel;
    using at least one metal hydroxide;
    using at least one metal halide;
    using at least one solvent;
    mixing at least one said metal hydroxide and at least one said metal halide in at least one said solvent under continuous stirring at a temperature in the range of 80 to 120° C. to obtain the ionic liquid composition in the form of ionic liquid clathrate;
    wherein said solvent is selected from the group consisting of benzene, and toluene; and
    wherein said ionic liquid clathrate is represented by Formula (I):
    M1•M2•M3• . . . •Mn•solvent (Formula (I))
    wherein M1 is at least one metal hydroxide;
    M2, M3, . . . , Mn are metal halides;
    n is in the range of 2 to 20; and
    the dot (•) between M1, M2, M3, Mn and solvent represents at least one coordinate covalent bond and weak van der waal's force,
    wherein the at least one said metal hydroxide is selected from the group consisting of aluminum hydroxide, chromium hydroxide, iron hydroxide, cobalt hydroxide, nickel hydroxide, cupric hydroxide, tin hydroxide, and lead hydroxide, and
    wherein the at least one said metal halide is selected from the group consisting of aluminum chloride, ferric chloride, aluminum bromide, titanium tetrachloride, cupric chloride, magnesium chloride, copper chloride, zinc chloride, cuprous chloride, and chromium chloride.

2. The process as claimed in claim 1, wherein said ionic liquid clathrate is a chemical substance consisting of a lattice of the metal hydroxide and the metal halide that traps or contains molecules of solvent.

3. The process as claimed in claim 1, wherein said ionic liquid clathrate comprising the metal hydroxide.

4. The process as claimed in claim 1, wherein said ionic liquid composition comprises:
    said metal hydroxide in an amount in the range of 3% to 40% by weight of the composition,
    said metal halide in an amount in the range of 8% to 80% by weight of the composition; and
    said at least one solvent in an amount in the range of 10% to 70% by weight of the composition.

5. The process as claimed in claim 1, wherein the metal of at least one said metal hydroxide and the metal of at least one said metal halide are same or are different.

6. The process as claimed in claim 1, wherein said ionic liquid composition has a viscosity ranging from 3 cP to 500 cP and density ranging from 1.00 to 2.50.

7. The process as claimed in claim 1, wherein 1 mole of aluminium hydroxide is heated with at least 1.5 moles of aluminium chloride in a benzene at a temperature of 80° C. to obtain the ionic liquid composition.

* * * * *